(12) United States Patent
Srbinoska (10) Patent No.: US 12,156,803 B2
(45) Date of Patent: Dec. 3, 2024

(54) INTRAOCULAR LENSES WITH INTEGRATED LOCKING UNIT FOR A HAPTIC CLAMP

(71) Applicant: CARL ZEISS MEDITEC AG, Jena (DE)

(72) Inventor: Hristina Srbinoska, Kleinmachnow (DE)

(73) Assignee: CARL ZEISS MEDITEC AG, Jena (DE)

( * ) Notice: Subject to any disclaimer, the term of this patent is extended or adjusted under 35 U.S.C. 154(b) by 67 days.

(21) Appl. No.: 17/995,744

(22) PCT Filed: Mar. 29, 2021

(86) PCT No.: PCT/EP2021/058127
§ 371 (c)(1),
(2) Date: Oct. 7, 2022

(87) PCT Pub. No.: WO2021/204576
PCT Pub. Date: Oct. 14, 2021

(65) Prior Publication Data
US 2023/0122656 A1   Apr. 20, 2023

(30) Foreign Application Priority Data
Apr. 7, 2020   (DE) .................... 10 2020 109 639.9

(51) Int. Cl.
*A61F 2/16*   (2006.01)
(52) U.S. Cl.
CPC ........ *A61F 2/16* (2013.01); *A61F 2002/1681* (2013.01); *A61F 2002/16902* (2015.04);
(Continued)

(58) Field of Classification Search
None
See application file for complete search history.

(56) References Cited

U.S. PATENT DOCUMENTS 3,906,551 A * 9/1975 Otter ......................... A61F 2/16
623/6.4
4,280,232 A    7/1981 Hummel
(Continued)

FOREIGN PATENT DOCUMENTS

EP   0 175 972 A1   4/1986

OTHER PUBLICATIONS

Office Action of German Application No. 10 2020 109 639.9, mailed Mar. 9, 2021.
(Continued)

*Primary Examiner* — Leslie A Lopez
(74) *Attorney, Agent, or Firm* — Alston & Bird LLP (57) ABSTRACT

Provided is an intraocular lens having at least one optical part and having a haptic coupled to the optical part, and having an optical principal axis that passes through a front side and a back side of the optical part, the haptic comprising at least one haptic loop, wherein a coupling element of the intraocular lens is integrated on the haptic loop and a mating coupling element of the intraocular lens is integrated on the optical part or on a connector coupled to the optical part, the coupling element being formed for direct coupling to the mating coupling element and, in the coupled state of coupling element and mating coupling element, an outer edge segment of the haptic loop being arranged at a radially shorter distance from the optical part than in the case of the uncoupled state of coupling element and mating coupling element.

7 Claims, 3 Drawing Sheets

(52) U.S. Cl.
CPC ............... *A61F 2220/0025* (2013.01); *A61F 2230/0043* (2013.01); *A61F 2250/0008* (2013.01)

(56) References Cited

U.S. PATENT DOCUMENTS

| | | | |
|---|---|---|---|
| 4,504,981 A | | 3/1985 | Walman |
| 4,513,456 A | * | 4/1985 | White ..................... A61F 2/16 623/6.51 |
| 4,615,701 A | * | 10/1986 | Woods ................ A61F 2/1613 623/6.45 |
| 4,704,125 A | * | 11/1987 | Ruminson ................ A61F 2/16 623/6.45 |
| 4,737,322 A | * | 4/1988 | Bruns .................... B29C 33/12 623/6.43 |
| 4,969,897 A | * | 11/1990 | Kalb ..................... A61F 2/161 623/6.45 |
| 2002/0022882 A1 | | 2/2002 | Morgan et al. |

OTHER PUBLICATIONS

PCT International Search Report and Written Opinion of the International Searching Authority, WIPO Application No. PCT/EP2021/058127, mailed Jul. 7, 2021.

\* cited by examiner

INTRAOCULAR LENSES WITH INTEGRATED LOCKING UNIT FOR A HAPTIC CLAMP

CROSS-REFERENCE TO RELATED APPLICATIONS

The present application is a national phase entry of International Application No. PCT/EP2021/058127, filed Mar. 29, 2021, which claims priority to German Patent Application No. 10 2020 109 639.9, filed Apr. 7, 2020, which are each incorporated herein by reference in their entirety.

TECHNICAL FIELD

One aspect of the invention relates to an intraocular lens having at least one optical part and having one haptic coupled to the optical part. The intraocular lens has a principal optical axis that passes through a front side and a back side of the optical part. The haptic has at least one first haptic loop.

PRIOR ART

Intraocular lenses are known in various embodiments. They have an optical part. It is adjoined by a haptic at a radially outer edge. The haptic can have one of many different designs. Haptics where at least one haptic loop is arranged projecting from the optical part are known. The haptic loop may have a strand-like design. It can merge into the optical part at its two ends. Moreover, embodiments of a haptic loop that merges into the optical part at only one end are also known. The other end is cantilevered. In this respect, such haptic loops are also referred to as C-loops.

Intraocular lenses that are implanted into a capsular bag of an eye may also grow together with the said capsular bag. In the process, the haptic grows together with the capsular bag. In that case, the intraocular lens is arranged quite fixed in terms of position and immovably on the capsular bag. It is difficult to change the position of the lens when the lens is in the capsular bag in such a state. In this context, the haptic grown together with the capsular bag must initially be detached in order to be able to carry out a desired rotation. Such an adjustment of position in the capsular bag may arise especially in the case of intraocular lenses with a specific imaging property, for example a toric intraocular lens. This is implemented to the effect of being able to correct the astigmatism, which is intended to be corrected by the toric intraocular lens, to the best possible extent.

U.S. Pat. No. 4,504,981 has disclosed an intraocular lens with an optical part and a haptic which has two haptic loops. A hole is formed in one haptic loop. Moreover, a hole is formed in the optical part. Using an auxiliary tool that is separate from the intraocular lens, it is possible to engage in the hole in the haptic loop. The haptic loop can be pulled toward the optical part. If the auxiliary tool is then additionally inserted into the hole in the optical part, it is possible to secure the haptic loop in the position relative to the optical part that the said haptic loop has been pulled into by means of the auxiliary tool. However, this requires an auxiliary tool, which is not a constituent part of the intraocular lens, to be used as a separate holding component in order even to be able to secure the holding loop to the optical part. Such a configuration always requires a separate auxiliary and holding tool of this type.

Moreover, securing the position of the holding loop relative to the optical part is only provided for the actual implantation procedure of the intraocular lens in the prior art. This is because the intention in that case is to avoid the relatively delicate and cantilevered holding loop being undesirably compressed or undesirably altered in terms of its orientation. Therefore, the solution provided there is not suitable as a matter of principle for a sparing detachment of an already implanted intraocular lens, which has grown together with a capsular bag, from the said capsular bag in order to be able to bring about a rotation of the implanted intraocular lens in the capsular bag.

SUMMARY OF THE INVENTION

It is an object of the present invention to develop an intraocular lens which allows improved securing positioning of components of the intraocular lens relative to one another.

This object is achieved by an artificial intraocular lens according to the features of claim 1.

One aspect of the invention relates to an intraocular lens. The intraocular lens comprises at least one optical part. Moreover, the intraocular lens comprises a haptic. The haptic is coupled to the optical part. In particular, it is directly connected to the optical part. The intraocular lens has a principal optical axis that passes through a front side and a back side of the optical part, especially centrally through the middle. The haptic has at least one first haptic loop. A coupling element of the intraocular lens is integrated on the haptic loop. Consequently, the coupling element is formed in one piece with the haptic loop. A mating coupling element of the intraocular lens is integrated on the optical part or on a connector coupled to the optical part. Consequently, a mating coupling element may also be formed on a connector that fully or partially surrounds the optical part. The mating coupling element is formed in one piece with the optical part or the connector. The connector has no optical imaging property. It directly adjoins the peripheral edge of the optical part. The connector in the form of a segment piece may be a portion of a ring that runs around the optical part. However, the connector may also be a connector with any desired geometric design on the optical part, with the connector not forming a ring geometry or a portion of a ring. The connector can be a component of the intraocular lens that is separate from the haptic. The connector may be designed so as to run completely around the optical part, for example as a ring, or so as to run only partly around the optical part. In particular, the connector is arranged at the equator of the optical part. Therefore, the connector is preferably arranged so as to run around at least portions of the principal optical axis in particular. In particular, the connector is formed in one piece with the optical part.

The coupling element is designed for direct coupling with the mating coupling element. In the coupled state of coupling element and mating coupling element, an outer edge segment of the haptic loop is arranged at a shorter radial distance from the optical part than in the uncoupled state of coupling element and mating coupling element. Hence, a locking unit integrated in the intraocular lens is created by the coupling element and the mating coupling element. This allows a haptic loop to be held in the defined position relative to the optical part. In the coupled state, these two integrated elements are directly coupled to one another. As a result, the coupled state can be held permanently by way of these elements themselves. As a result, there is no need for separate holding parts in order to hold a coupled state defined in this way, in the case of which the haptic loop is fixed relative to the optical part in a radially inwardly pulled position. As a result of directly coupling the coupling element and the mating coupling element, this configuration also makes it possible to avoid damage to the intraocular lens, especially in the optical part. This risk may occur whenever a holding part external to the intraocular lens is required for maintaining such a coupling position between the holding loop and the optical part. Since an outer edge segment of the haptic loop is pulled radially with respect to the first optical part in the coupled state, and said outer edge segment is consequently radially pretensioned, corresponding forces act on the coupling element and the mating coupling element. However, these can be absorbed by these coupled elements. On account of the design of the coupling element and mating coupling element, it is possible to avoid damage, firstly to these elements and secondly to the optical part.

In the uncoupled state between the coupling element and the mating coupling element, the haptic loop is arranged in a base position relative to the optical part. In this base position, an outer edge segment of the haptic loop is radially further away from the optical part than in the case of the coupled state of the coupling element and mating coupling element.

Such a configuration of an intraocular lens itself very advantageously allows a simpler detachment of a haptic that has grown together with the capsular bag. In this context, all that is still required is to pull the coupling element to the optical part using an auxiliary tool. In particular, this brings about a detachment of the overgrown haptic loop from the capsular bag. By virtue of this auxiliary tool then being used to bring the coupling element into such a position where it couples with the mating coupling element, this coupled state can be maintained without further actuation and without further presence of the auxiliary tool. Thus, the auxiliary tool is only required for the action of bringing the coupling element to the mating coupling element. The coupled state subsequently attained is then maintained only by the coupling element and the mating coupling element of the intraocular lens itself.

In particular, a haptic loop has at least one end directly connected to the optical part or the connector at a first point, especially non-detachably connected therewith without being destroyed. The coupling element is arranged on the haptic loop, in particular produced in one piece therewith, at a distance from this end of the haptic loop. Independently of the coupled state of the coupling element with the mating coupling element and independently of the decoupled state of the coupling element with the mating coupling element, the end is permanently connected to the optical part or the connector, in particular without a change in the location of the end relative to the optical part or connector. Provision may be made for a haptic loop to end at the connector or the optical part with only one end and for the other end of the haptic loop to be arranged in cantilevered fashion. Should a haptic loop in one exemplary embodiment have a further end that is connected to the optical part or the connector at a second position that differs from the first position, the corresponding explanations as presented above for the first end apply in relation to the coupling element. Then, both ends end at the connector or the optical part, but at different points in particular. The coupling point between the coupling element and the mating coupling element is formed spaced apart from, and independent of, the first position or the second position on the optical part or on the connector. The optical part is formed in one piece with at least one haptic loop, in particular all haptic loops, of the lens. This means that the optical part, optionally with the connector, is manufactured together with the haptic loop during the basic production process.

A coupling element is a component part of a haptic loop that differs from an end of a haptic loop. A coupling element is arranged on a haptic loop at a distance from one end of the said haptic loop.

In an exemplary embodiment, the intraocular lens is formed with only a single, one-piece optical part. In particular, this optical part is formed in one piece with the haptic. The intraocular lens then has a one-piece form as a whole.

In another exemplary embodiment, the intraocular lens is formed with a first, one-piece optical part. This first optical part can be formed in one piece with the haptic. The intraocular lens comprises a second optical part in this exemplary embodiment. This second optical part is separate from the first optical part. The second optical part forms an optical system of the intraocular lens together with the first optical part. In this exemplary embodiment, provision can be made for the two optical parts to rest against one another. They may be arranged in series in the direction of the principal optical axis. The at least two optical parts may be interconnected by way of a connecting element, for example a connecting loop, of the intraocular lens. In the exemplary embodiment, provision can be made for the at least one mating coupling element to be formed in the second optical part. In particular, the second optical part has a larger embodiment than the first optical part in a direction perpendicular to the principal optical axis. As a result, the second optical part has a radial protrusion in comparison with the first optical part. In particular, the at least one mating coupling element is formed in this protrusion.

In a further exemplary embodiment, the intraocular lens comprises an optical part and a haptic separate therefrom. In this exemplary embodiment, the two components do not have a one-piece design. In particular, the haptic forms a support skeleton with a haptic loop and a receptacle for the optical part. This receptacle may be a ring or a segment piece. The optical part is insertable into the receptacle such that the optical part is at least sectionally gripped at its equator by the receptacle and held against the latter. The at least one mating coupling element is formed in the optical part. However, it may also be formed in the receptacle.

The coupling element comprises a connecting part, by means of which the coupling element is directly connected to the haptic loop. Moreover, the coupling element comprises a coupling web. This coupling web is formed on the end face of the connecting part. In particular, the coupling web is provided for direct engagement in the mating coupling element. In such a configuration, the coupling element and the mating coupling element engage with one another. Hence, a mechanical, engaging operative connection is created as an interlock. This creates a particularly simple yet mechanically loadable direct connection between these two elements.

The connecting part creates a stable attachment unit to the haptic loop. Consequently, a loadable attachment site is created at the interface between the haptic loop and the coupling element. This prevents the coupling element from tearing off the haptic loop. Since corresponding tensile forces also act precisely at this position when the intention is to detach the haptic loop from its grown together state with the capsular bag, such a configuration is advantageous in this respect.

Moreover, this connecting part consequently also serves as a robust and loadable mount for the coupling web.

The connecting part comprises at least one connecting bar. The latter extends projecting from an inner side of the haptic loop toward the optical part in the radial direction with respect to the principal optical axis. In this case, the inner side of the haptic loop faces the optical part. As a result of such an attachment site and orientation of this connecting bar, it is possible to further assist the aforementioned advantages. Especially on account of a straight-line design of the connecting bar it is also possible to very advantageously transfer the tensile forces of an auxiliary tool from the connecting part to the haptic loop. This also facilitates pulling in a very straight line and a direct force transfer. It is also simple to produce the connecting bar in its straight-line configuration. A particularly simple design is realized.

In particular, when considered in the direction of the principal optical axis, the connecting bar is thinner than the haptic loop on which the connecting bar ends.

In an exemplary embodiment, the connecting bar and the coupling web formed on its end side form an L-shaped part in cross section. The aforementioned advantages particularly come to bear in this context. This part has a simple design. It is mechanically stable and correspondingly loadable. Nevertheless, the base limb of the L-shape forms a simple coupling web, which first of all can easily be gripped by an auxiliary tool in order thus to very directly transfer a tensile force from the auxiliary tool to the connecting bar and, from there, to the haptic loop. Secondly, this L-shape also enables simple coupling with the mating coupling element. Only this coupling web in the form of an L-limb needs to engage in the mating coupling element in order to attain and also maintain the coupled state. In this case, the L-shape also forms a configuration that remains very dimensionally stable. Consequently, the coupled state, too, is kept permanently stable. The longer L-limb is formed by the connecting bar.

In the uncoupled state, the connecting part is arranged in cantilevered fashion between the coupling element and the mating coupling element. In this uncoupled state, the connecting part is oriented in the direction of the optical part. In this uncoupled state, the connecting part is arranged without being in contact with the optical part. This positioning and orientation yields advantages in respect of the handling with an auxiliary tool on the one hand and in respect of maintaining the coupled state on the other hand.

In an exemplary embodiment, the coupled state is held independently only by means of the coupling element and the mating coupling element by way of a direct engagement of said elements, without further external holding parts. This allows a connection very much reduced in terms of number of components but nevertheless mechanically loadable and stable.

An exemplary embodiment provides for the coupling element to comprise a connecting part, in particular a straight connecting bar, by means of which the coupling element is directly connected to the haptic loop. A magnet is arranged on this connecting part. The mating coupling element comprises an opposing magnet or is an opposing magnet, and so the coupled state is maintained by the magnetic holding force of the two magnets. Such a configuration creates an alternative to a mechanical engagement of components of the locking unit. The two magnets magnetically interact when the coupling element is pulled or guided to the optical part. The magnetic attractive forces produced in the process then form a holding force, by means of which the holding loop is held in a fixed position relative to the optical part in the coupled state of the coupling element and the mating coupling element.

In an exemplary embodiment, a magnet is produced by injection molding with the haptic loop. Alternatively, the magnet can be produced as a 3-D printed component with the haptic loop.

Provision can be made for the entire intraocular lens to be formed in one piece. It is also possible that the haptic is produced independently of the optical part and the optical part is then inserted into or held against this haptic. In this context, the optical part may be formed from a polymer material. The haptic may be realized as an injection molded component or as a 3-D printed component. However, it is also possible that the entire intraocular lens including the optical part and the haptic is produced from one piece, in particular from a polymer material.

An exemplary embodiment provides for the coupling element to comprise a connecting part, by means of which the coupling element is directly connected to the haptic loop. The connecting part comprises at least two separate, in particular straight connecting bars. These at least two connecting bars are connected to an inner side of the haptic loop, in particular in one-piece fashion, at different points. In an advantageous embodiment, these two connecting bars project from an inner side of the haptic loop at different points and are oriented in the direction of the optical part.

In an advantageous exemplary embodiment, these connecting bars are interconnected at their ends that face the optical part. In particular, they may be formed in one piece with one another at these ends. This yields a coupling element that is connected to the haptic loop at different points. This allows a greater tensile force to be applied, and so the haptic loop can be reliably removed from the capsular bag even in the case of significant growing together. The rotation of the intraocular lens relative to the capsular bag, required and desired in that case, is then more easily possible.

The mating coupling element is a through hole in an exemplary embodiment. This means that it is designed to be fully passable. As a result, it is also possible to introduce a liquid through this through hole. This renders it easily possible to introduce this liquid between the capsular bag and the optical part of the intraocular lens.

Further features of the invention are evident from the claims, the figures and the description of the figures. The features and combinations of features mentioned in the description above and the features and combinations of features mentioned in the description of the figures below and/or shown only in the figures can be used not only in the respectively specified combination but also in other combinations, without departing from the scope of the invention. The invention shall thus also be considered to include and disclose configurations of the invention that are not shown and elucidated explicitly in the figures, but arise from and can be created through separate combinations of features from the configurations elucidated. Disclosure shall also be considered to extend to configurations and combinations of features that thus do not have all the features of an independent claim as originally worded. Disclosure shall additionally be considered to extend to embodiments and combinations of features, in particular by virtue of the embodiments explained above, which go beyond or depart from the combinations of features set out in the dependency references of the claims.

The specific values indicated in the documents for parameters and indications concerning ratios of parameters or parameter values for the definition of exemplary embodiments of the eye lens should be considered to be concomitantly encompassed by the scope of the invention even in the context of deviations, for example on account of measurement errors, system faults, DIN tolerances, etc., which is also understood to mean explanations relating to substantially corresponding values and indications.

BRIEF DESCRIPTION OF THE DRAWINGS

Exemplary embodiments of the invention will be explained in more detail below with reference to schematic drawings. In the drawings.

Preferred exemplary embodiments of the invention

In the figures, identical or functionally identical elements are given the same reference signs.

Figure 1A:
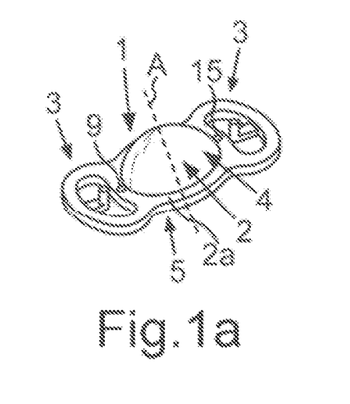
FIG. 1a shows a perspective representation of a first exemplary embodiment of an intraocular lens according to the invention.

FIG. 1a shows a perspective representation of a first exemplary embodiment of an artificial eye lens, which is an intraocular lens 1. The intraocular lens 1 comprises an optical part 2 and, adjacent thereto, a haptic 3. The intraocular lens 1 is foldable and may be introduced into an eye through a small incision. The optical part 2, which is essential for the optical imaging property of the eye lens 1, comprises a principal optical axis A. Moreover, when viewed in the direction of this principal optical axis A, the optical part 2 comprises a first optical surface or side 4, which may be a front side, and comprises opposite thereto a second optical surface or side 5, which may be a back side. In the implanted state of the eye lens 1 in the eye, the exemplary front side faces the cornea, whereas the back side faces away from this cornea.

Figure 1B:
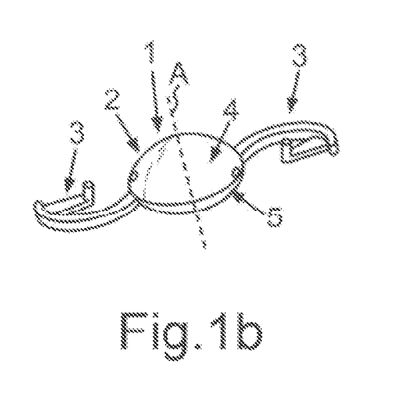
FIG. 1b shows a perspective representation of a further exemplary embodiment of an intraocular lens according to the invention.

FIG. 1b shows a perspective representation of a further exemplary embodiment of an artificial eye lens in the form of an intraocular lens 1. Said lens differs from the embodiment in FIG. 1a by way of the different haptic 3. The intraocular lens 1 is held in the eye by means of the haptic 3.

The sides 4 and 5 are curved in particular in a non-planar fashion, in particular convexly, in the embodiments. The sides 4 and/or 5 may also be concave or plane. On at least one side 4, 5, a diffractive profile may be formed on this convex basic shape.

Figure 2:
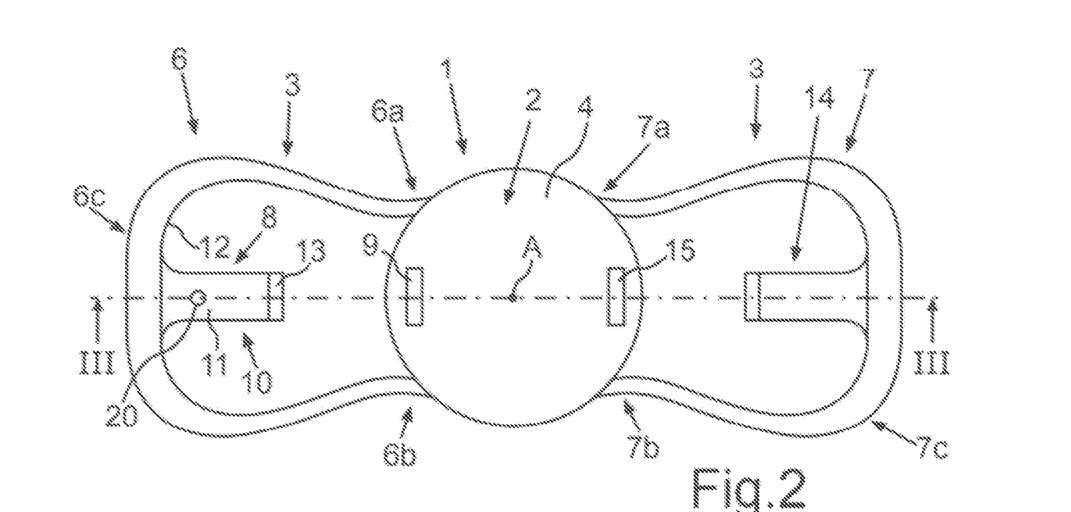
FIG. 2 shows a plan view of an exemplary embodiment of an intraocular lens according to the invention in an uncoupled state between a coupling element and a mating coupling element.

FIG. 2 shows a schematic plan view of the intraocular lens 1 according to the exemplary embodiment in FIG. 1a. In the exemplary embodiment, the haptic 3 comprises a first haptic loop 6 and a second haptic loop 7. The two separate haptic loops 6 and 7 are connected to the optical part 2 at different circumferential positions. The haptic loop 6 has a strand-like embodiment in the exemplary embodiment shown. With a first end 6a, it is connected to the optical part 2. It is likewise connected to the optical part 2 by way of an opposite second end 6b. The exemplary embodiment provides for a corresponding situation with regards to ends 7a and 7b of the second haptic loop 7. The haptic loops 6, 7 are U-shaped in the exemplary embodiment.

A coupling element 8 is integrated on the first haptic loop 6. This means that this coupling element 8 is formed in one piece with the haptic loop 6. A mating coupling element 9 is formed in the optical part 2. By way of example, the mating coupling element 9 could be a through hole. However, it could also be a simple recess or depression. In particular, it could also be a blind hole.

The coupling element 8 is designed for direct coupling with the mating coupling element 9. When considered in the radial direction with respect to the principal optical axis A, the coupling element 8 and the mating coupling element 9 are designed such that, in their coupled state, the haptic loop 6 is held in a position closer to the optical part 2 than in the uncoupled position or uncoupled state shown in FIG. 2. It is evident that the coupling element 8 has a connecting part 10. By way of this connecting part 10, which has at least one connecting bar 11 in this case, the coupling element 8 is directly connected to an inner side 12 of the haptic loop 6, in particular formed in one piece therewith. Moreover, the connecting part 8 comprises a coupling web 13. The coupling web 13 is formed on the end face of the connecting part 10. In particular, the coupling web 13 is arranged at that end of the connecting part 10 which faces the optical part 2. In particular, the connecting bar 11 has a straight embodiment. As is evident, it extends from the inner side 12 toward the optical part 2. In particular, the connecting bar 11 is formed without a cavity. The connecting bar 11 projects from the inner side 12 and extends in the direction of the optical part 2.

In the uncoupled state, as shown in FIG. 2, the coupling element 8 is arranged at a distance from and without being in contact with the optical part 2. Advantageously, a correspondingly formed further coupling element 14 is formed on the second haptic loop 7 in the exemplary embodiment. It is formed to couple with a further mating coupling element 15 formed in the optical part 2. The exemplary embodiment shown in FIG. 2 differs slightly from the intraocular lens 1 according to FIG. 1a. An additionally peripheral connector 2a is provided in FIG. 1a. This connector 2a, peripheral in this case, surrounds the optical part 2 and has no optical imaging function. This peripheral connector 2a at least partly surrounds the optical part 2 in the circumferential direction about the principal optical axis A. In particular, the connector 2a extends over at least one segment piece or one ring segment, which is arranged at the equator of the optical part 2 in the region of the haptic 3. In contrast to FIG. 2, the mating coupling element 9 is formed in this connector 2a in the example of FIG. 1a. Accordingly, the mating coupling element 15 is also formed in this connector 2a. The connector 2a can be in the form of a ring or a segment piece.

The hole geometry of the mating coupling element 9, 15 may be without corners, for example round or oval. Its hole geometry may also be polygonal, for example quadrilateral. The geometry of the coupling element 8, 14, in particular of the coupling web 13, may be without corners or polygonal. In particular, the geometry of the coupling elements 8, 14 is adapted to match the geometry of the mating coupling elements 9, 15. This enables simple and accurate bringing together.

Figure 3:
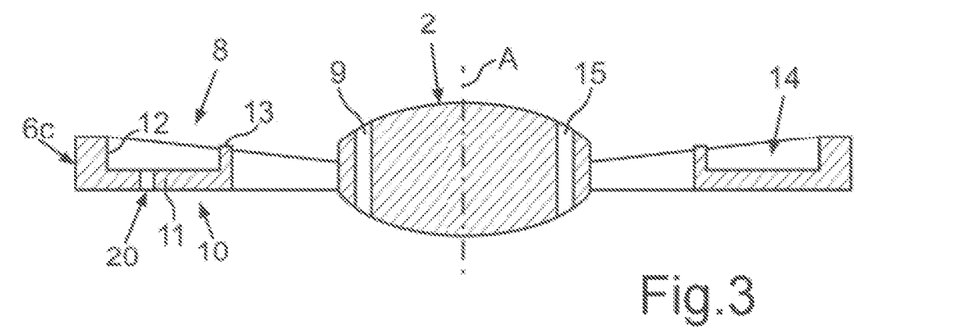
FIG. 3 shows a sectional representation through the intraocular lens according to FIG. 2.

In a sectional representation along the cut line III-III of FIG. 2, FIG. 3 depicts the uncoupled state of the intraocular lens 1 in relation to the coupling element 8 with the mating coupling element 9. It is evident that the coupling web 13 axially protrudes beyond the connecting bar 11. The L-shape of the coupling element 8 is shown in FIG. 3.

Figure 4:
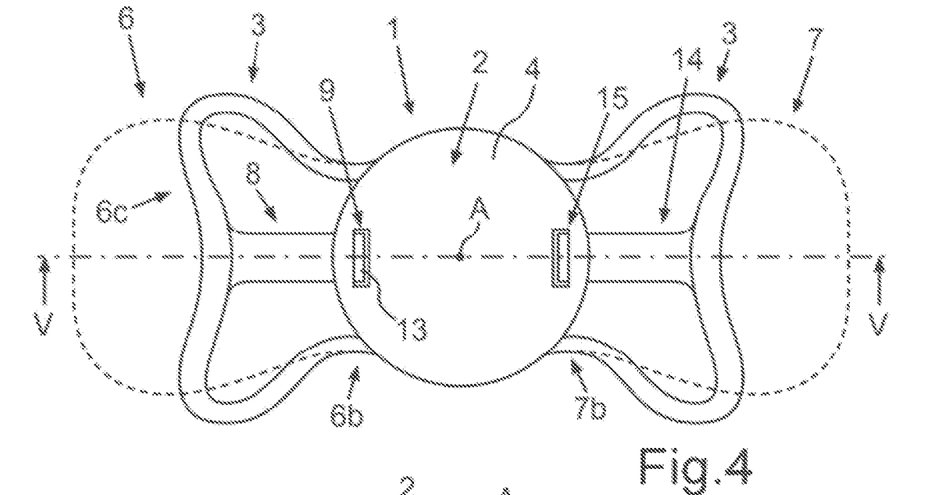
FIG. 4 shows a plan view of the intraocular lens according to FIG. 2, but in a coupled state between a coupling element and a mating coupling element.

FIG. 4 shows the intraocular lens 1 according to FIG. 2 and FIG. 3 in a plan view. However, this shows the coupled state between the coupling element 8 and the mating coupling element 9. Likewise, this shows the coupled state between the coupling element 14 and the mating coupling element 15.

To achieve this coupled state, the coupling element 8 can be pulled toward the mating coupling element 9 using an auxiliary tool not shown here when proceeding from the representation in FIGS. 2 and 3. This then also causes the coupling element 8 to be coupled with the mating coupling element 9.

By way of example, the auxiliary tool may have a hook which can be used to engage behind the coupling web 13 and pull the latter toward the mating coupling element 9. Considered in general, provision can also be made for the coupling element 8 to have an engagement region 20. The auxiliary tool can engage into the latter in order to pull the coupling element 8 to the mating coupling element 9. By way of example, the engagement region 20 may be formed in the connecting bar 11. It may be a blind hole or a through hole. In particular, the engagement region 20 is formed at a distance from the coupling web 13. The coupling element 14 may also have a corresponding engagement region.

Figure 5:
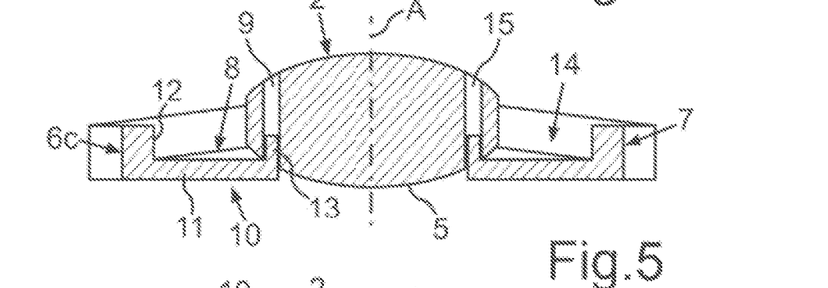
FIG. 5 shows a sectional representation through the intraocular lens according to FIG. 4.

As is evident in this respect from the sectional representation in FIG. 5, which shows a cut along the cut line V-V in FIG. 4, the coupling web 13 engages in this mating coupling element 9. Therefore, this brings about an axially overlapping engagement between the mating coupling element 9 and the coupling web 13. What is also obtained thereby is that an outer edge segment 6c of the first haptic loop 6 is arranged at a smaller radial distance from the optical part 2 than in the uncoupled state according to FIG. 2 and FIG. 3. The same may also arise for an outer edge segment 7c of the haptic loop 7. Consequently, this outer edge segment 6c is pulled toward the optical part 2. As a result of the coupled state between the coupling element 8 and the mating coupling element 9, this position which has been displaced toward the optical part 2 is also maintained in permanently fixed fashion. The coupling web 13 is hooked into this mating coupling element 9. Consequently, the intraocular lens 1 has an integrated locking unit, which comprises the coupling element 8 and the mating coupling element 9. In particular, the coupling element 14 and the mating coupling element 15 are also constituent parts of this locking unit.

Figure 6:
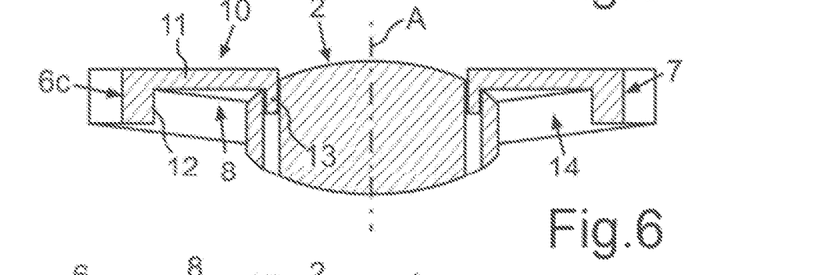
FIG. 6 shows a further sectional representation corresponding to the view in FIG. 5, but in an alternative of a coupled state between a coupling element and a mating coupling element to what is shown in FIG. 5.

FIG. 6 shows an alternative embodiment in a sectional representation analogous to FIG. 5. In the latter, the coupling web 13 consequently does not engage into the mating coupling element 9 from the second optical side 5 but engages into the mating coupling element 9 from the first optical side 4.

Figure 7:
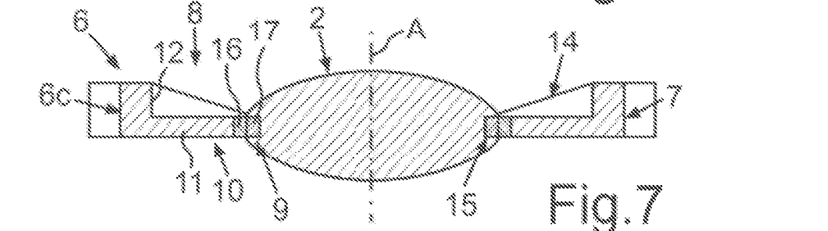
FIG. 7 shows a sectional representation of an exemplary embodiment of an intraocular lens in a coupled state between a coupling element and a mating coupling element, with the coupling element and the mating coupling element being designed alternatively to the embodiments according to FIG. 2 to FIG. 6.

FIG. 7 shows a further exemplary embodiment in a sectional representation. In contrast to FIG. 2 to FIG. 6, no coupling web 13 is provided for here. Instead, the connecting part 10 is formed in particular with a connecting bar 11. A magnet 16 is arranged at the end thereof facing the optical part 2. An opposing magnet 17 is arranged in the optical part 2. FIG. 7 shows the already coupled state between the magnets 16 and 17. Hence, a coupling is also formed between the coupling element 8 and the mating coupling element 9. A preferably present further coupling element 14 and a further present mating coupling element 15 may also have a corresponding design.

In a further exemplary embodiment, provision can be made for a coupling element 8 with a coupling web 13 to be present, which mechanically engages directly in a mating coupling element 9. A further coupling element 14 may be provided, which then comprises such a magnet 16. In this embodiment, the mating coupling element 15 may then have a corresponding opposing magnet 17. Consequently, different concepts of coupling elements and mating coupling elements are realized in an intraocular lens 1.

Figure 8:
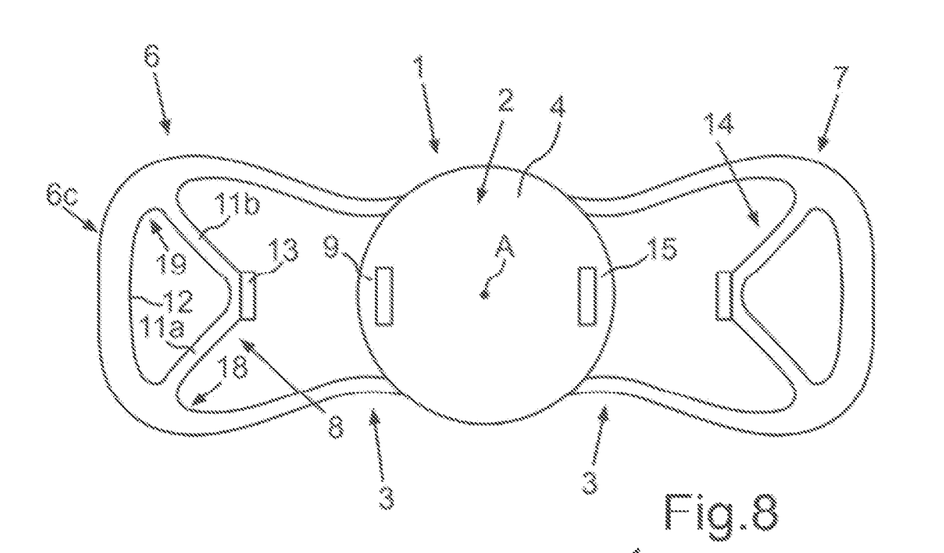
FIG. 8 shows a schematic plan view of a further exemplary embodiment of an intraocular lens in the uncoupled state of a coupling element and a mating coupling element.

FIG. 8 shows a further exemplary embodiment of an intraocular lens 1 in a simplified plan view. In contrast to the previous examples, this exemplary embodiment provides for the coupling element 8 to have not only one connecting bar 11 but two separate connecting bars 11a and 11b. Additionally, more than two such separate connecting bars may be realized. As is evident in FIG. 8, the first connecting bar 11a merges into the inner side 12 of the first haptic loop 6 at a first point 18. The second connecting bar 11b merges into the inner side 12 at a second point 19 differing therefrom. In particular, provision can be made for the two connecting bars 11a and 11b to form a V shape. The two ends of the connecting bars 11a and 11b which face the optical part 2 can be interconnected. They can be formed together in one piece. The coupling web 13 or a magnet 16 may be arranged at this merged end. In the case of an appropriate force acting on the coupling element 8 in the direction of the principal optical axis A, such a configuration can bring about a pulling of an outer edge segment 6c of the first haptic loop 6 toward the optical part 2. This can be carried out with a higher tensile force than in the previously described exemplary embodiments.

Figure 9:
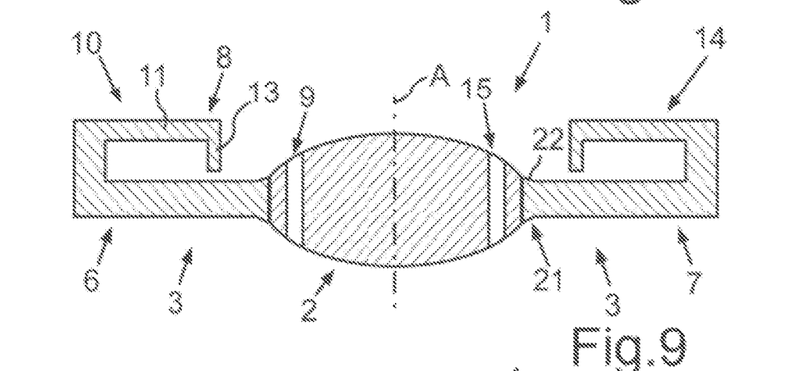
FIG. 9 shows a sectional representation of a further exemplary embodiment of an intraocular lens in the uncoupled state of coupling elements and a mating coupling element.

FIG. 9 shows a further exemplary embodiment of an intraocular lens 1 in a sectional representation. The optical part 2 and the haptic 3 are formed separately in this exemplary embodiment. This means that they are independent components in each case. The haptic 3 comprises the haptic loops 6, 7. Furthermore, the haptic 3 comprises a receptacle 21. In the exemplary embodiment, the latter is a fully closed circumferential ring 22. The ring 22 may also be a connector 2a, as shown in FIG. 1a. The optical part 2 is accommodated and held in the ring 22. The haptic 3 with the haptic loops 6, 7 and the ring 22 forms a support skeleton. The haptic 3 is designed in one piece.

Figure 10:
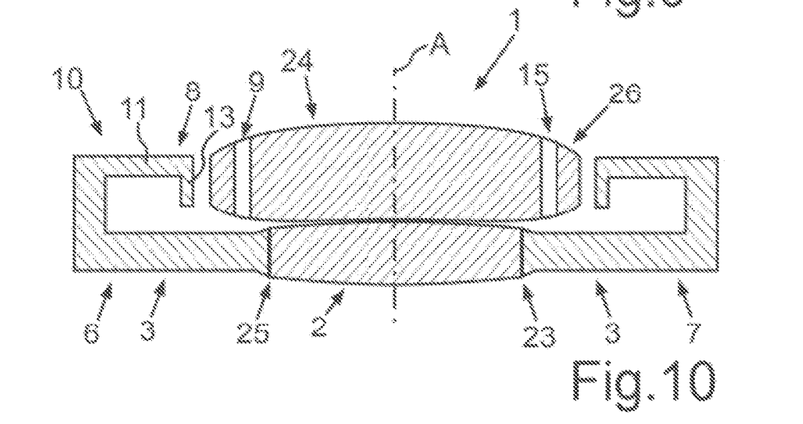
FIG. 10 shows a sectional representation of a further exemplary embodiment of an intraocular lens in the uncoupled state of coupling elements and a mating coupling element.

FIG. 10 shows a further exemplary embodiment of an intraocular lens 1 in a sectional representation. The intraocular lens 1 comprises a base lens 23. The base lens 23 comprises a first optical part 2. The base lens 23 comprises a haptic 3. The haptic 3 comprises the haptic loops 6, 7. In relation to the orientation, these may be formed in accordance with the configuration in FIG. 9. These may also be arranged and oriented differently, just like the haptic loops 6, 7 in the exemplary embodiment of FIG. 9, for example like in FIGS. 3 and 5 or like in FIG. 8.

In the exemplary embodiment, the base lens 23 is preferably formed in one piece. Moreover, the intraocular lens 1 comprises a second optical part 24. This second optical part 24 is formed separately from the base lens 23. The second optical part 24, which also constitutes a lens, is arranged in series with the first optical part 2. As a result, an optical system 25 of the intraocular lens 1 is formed. In particular, the second optical part 24 may rest against the first optical part 2. The second optical part 24 is coupled to the first optical part 2 so as to be stable in terms of position (not depicted in FIG. 10). The second optical part 24 preferably has a larger embodiment than the first optical part 2. This means that the second optical part 24 has a larger embodiment than the first optical part 2 in a direction perpendicular to the principal optical axis A. This forms a radial protrusion 26 of the second optical part 24 in comparison with the first optical part 2. Preferably, at least one mating coupling element 9, 15 is formed in this protrusion 26.

An alternative with magnets, especially as in FIG. 7, may also be provided in the exemplary embodiments according to FIG. 9 or 10.

The invention claimed is:

1. An intraocular lens having at least one optical part and having a haptic coupled to the optical part, and having an optical principal axis that passes through a front side and a back side of the optical part, the haptic comprising at least one haptic loop,
    wherein a coupling element of the intraocular lens is integrated on the haptic loop and a mating coupling element of the intraocular lens is integrated on the optical part or on a connector coupled to the optical part, the coupling element being formed for direct coupling to the mating coupling element and, in a coupled state of the coupling element and the mating coupling element, an outer edge segment of the haptic loop being arranged at a radially shorter distance from the optical part than in the case of an uncoupled state of the coupling element and the mating coupling element, with the haptic loop having a first end directly connected to the optical part or the connector at a first point and a second end directly connected to the optical part or the connector at a second point, the coupling element being arranged on the haptic loop at a distance from the first end,
    with the coupling element comprising a connecting part, by means of which the coupling element is directly permanently connected to the haptic loop, and the coupling element having a coupling web formed on an end face of the connecting part, the coupling web being provided for direct engagement with the mating coupling element, and
    in the uncoupled state the connecting part being arranged in cantilevered fashion in a direction of the optical part and arranged so as not to be in contact with the optical part;
    wherein, in the uncoupled state of the coupling element and the mating coupling element, the first end and the second end of the haptic loop are directly connected to the optical part or the connector at the first point and the second point, respectively;
    wherein the haptic loop is further defined by a first arm segment and a second arm segment extending from respective portions of the outer edge segment to the first end at the first point and the second end at the second point, respectively.

2. The intraocular lens as claimed in claim 1, wherein the connecting part has at least one connecting bar which projects from an inner side of the haptic loop and which extends toward the optical part in a radial direction.

3. The intraocular lens as claimed in claim 2, wherein the connecting bar and the coupling web form a part with an L-shaped cross section.

4. The intraocular lens as claimed in claim 1, wherein the coupled state is held independently and without further external holding parts as a result of the direct engagement between the coupling element and the mating coupling element.

5. The intraocular lens as claimed in claim 1, wherein the mating coupling element is a through hole.

6. An intraocular lens having at least one optical part and having a haptic coupled to the optical part, and having an optical principal axis that passes through a front side and a back side of the optical part, the haptic comprising at least one haptic loop,
    wherein a coupling element of the intraocular lens is integrated on the haptic loop and a mating coupling element of the intraocular lens is integrated on the optical part or on a connector coupled to the optical part, the coupling element being formed for direct coupling to the mating coupling element and, in a coupled state of the coupling element and the mating coupling element, an outer edge segment of the haptic loop being arranged at a radially shorter distance from the optical part than in the case of an uncoupled state of the coupling element and the mating coupling element, with the haptic loop having a first end directly connected to the optical part or the connector at a first point and a second end directly connected to the optical part or the connector at a second point, the coupling element being arranged on the haptic loop at a respective distance from the first end and the second end,
    with the coupling element comprising a connecting part, by means of which the coupling element is directly permanently connected to the haptic loop, and the coupling element having a coupling web formed on an end face of the connecting part, the coupling web being provided for direct engagement with the mating coupling element, and
    wherein the connecting part has at least one straight connecting bar which projects from an inner side of the haptic loop and which extends toward the optical part in a radial direction;
    wherein, in the uncoupled state of the coupling element and the mating coupling element, the first end and the second end of the haptic loop are directly connected to the optical part or the connector at the first point and the second point, respectively;
    wherein the haptic loop is further defined by a first arm segment and a second arm segment extending from respective portions of the outer edge segment to the first end at the first point and the second end at the second point, respectively.

7. The intraocular lens as claimed in claim 6, wherein the connecting bar and the coupling web form a part with an L-shaped cross section.

* * * * *